| United States Patent [19] | [11] Patent Number: 4,876,378 |
| Van Sickle | [45] Date of Patent: Oct. 24, 1989 |

[54] RECOVERY OF DIALKYL NAPHTHALENE-2,6-DICARBOXYLATES FROM NAPHTHALENE-2,6-DICARBOXYLIC ACID-CONTAINING POLYESTERS

[75] Inventor: Dale E. Van Sickle, Kingsport, Tenn.

[73] Assignee: Eastman Kodak Company, Rochester, N.Y.

[21] Appl. No.: 197,232

[22] Filed: May 23, 1988

[51] Int. Cl.$^4$ ................... C07C 67/60; C07C 69/76
[52] U.S. Cl. ........................... 560/78; 560/79; 560/80
[58] Field of Search ....................... 560/78, 80

[56] References Cited

U.S. PATENT DOCUMENTS 3,488,298  1/1970  Miller ................... 560/80 X

FOREIGN PATENT DOCUMENTS 2041916  9/1980  United Kingdom .

Primary Examiner—Werren B. Lone
Assistant Examiner—Vera C. Clarke
Attorney, Agent, or Firm—S. E. Reiter; William P. Heath, Jr.

[57] ABSTRACT

A process for the formation and recovery of dialkyl naphthalene-2,6-dicarboxylates from poly-(alkylene naphthalene-2,6-dicarboxylate) polyesters. Alcoholysis of poly(ethylene naphthalene-2,6-dicarboxylate) in the presence of a transesterification catalyst on cooling yields solid dialkyl naphthalene-2,6-dicarboxylate which may be collected by filtration and further purified by recrystallization from xylenes. Novel alkyl hydroxyalkyl naphthalene-2,6-dicarboxylate compounds may be isolated from the filtrate and either reconverted to polyester or further alcoholized to dialkyl naphthalene-2,6-dicarboxylate.

22 Claims, No Drawings

RECOVERY OF DIALKYL NAPHTHALENE-2,6-DICARBOXYLATES FROM NAPHTHALENE-2,6-DICARBOXYLIC ACID-CONTAINING POLYESTERS

BACKGROUND OF THE INVENTION

1. Field of the Invention

The present invention relates to a method for the recovery of dialkyl naphthalene-2,6-dicarboxylates from naphthalene-2,6-dicarboxylic acid-containing polyesters by the alcoholysis of the polyesters. In one aspect, the invention pertains to the recycling of dialkyl naphthalene-2,6-dicarboxylates from polyester scrap which may be contaminated with other polyesters, polymers, or dyes. In another aspect, the invention relates to novel naphthalene dicarboxylate compounds.

2. Description of the Background

Poly(ethylene terephthalate) (PET) polyesters are well known as packaging materials. However, gaseous diffusion rates across barriers of PET are higher than desired for materials to be used in packaging carbonated beverages. It has become established that polyesters made from naphthalene-2,6-dicarboxylic acid (NDA) show superior properties to those made from the much more commonly available, and much less costly, terephthalic acid. In particular, the polyester formed from NDA and ethylene glycol, poly(ethylene naphthalene-2,6-dicarboxylate) (PEN), is superior to PET in the retention of gaseous molecules in bottles fabricated from these polyesters. That is, gaseous diffusion rates across barriers of PEN are less than the rates for similar configurations of PET. Packages fabricated from PEN are expected to be more desirable, particularly for carbonated beverages. However, PEN has a higher value and cost of manufacture than PET. It is thus desirable, from an economic standpoint, to be able to recover and recycle bottles made from PEN. It is also desirable, from an environmental viewpoint, to be able to recover and recycle bottles made from PEN. However, although a number of methods have been devised for the recovery and recycling of PET, there is no known method for the recovery and recycling of PEN.

Typically, PET is recycled by converting the polyester to its precursors, dimethyl terephthalate (DMT) and ethylene glycol (EG) by reacting the polymer with methanol in the presence of a transesterification catalyst. On cooling the reaction mixture, DMT precipitates and may be collected by filtration. The crude alcohol-wet DMT filter cake is then washed with alcohol. The washing step removes most of the catalyst, glycol, and side products, and the crude DMT cake is then distilled to remove alcohol and finally vacuum distilled to give pure DMT. This recovery process is complex and time consuming, and therefore greatly reduces the incentive for the recycling of PET. If the washing step is omitted, the transesterification catalyst present in the DMT filter cake catalyzes the production of polyester during the recovery process. Thus, omission of the washing step decreases the yield of DMT.

U.S. Pat. No. 3,488,298 discloses an alternative method wherey the DMT may be distilled directly from the reaction mixture without first filtering and washing. The reaction mixture is separated into its components by distillation, with the catalyzed production of polyester during the distillation is prevented by first adding a catalyst poison. The disclosed catalyst poisons include a number of phosphorus-containing compounds.

U.K. patent application No. 2,041,916 describes a method for improving the yield of DMT from the methanolysis of PET. The improvement comprises adding an alkaline transesterification catalyst to the filtrate obtained in the filtration step to catalyze the formation of DMT from the by-products of the initial methanolysis.

East German Pat. No. 116,251 describes the degradation of PET to polyesters which may be used in high quality fiber forming processes by reacting scrap PET with small quantities of alcohol at temperatures from 200° to 300° C. in an extrusion device.

Japanese Pat. Nos. 48 68,538 and 48 68,537 disclose a method for improving the yield of DMT by adding compounds such as ammonium hydroxide or alkali metal hydroxide or chloride to the cooled reaction mixture before filtration. Japanese Pat. No. 49 41,330 describes the alcoholysis of PET with ethylene glycol, and Japanese Pat. No. 50 82,028 teaches the alcoholysis of PET with a mixture of ethylene glycol and methanol in the presence of a transesterification catalyst.

Thus, the known methods for recovering and recycling PET either suffer from being impractical or involve complicated multi-step procedures. Further, it is not clear that any of the above-described methods would be applicable to the recovery and recycling of poly(alkylene naphthalene-2,6-dicarboxylate) resins. Thus, there is a need for a method for the recovery and recycling of poly(alkylene naphthalene-2,6-dicarboxylate) resins. In particular, there is a need for a method for the recovery and recycling of PEN.

Since it is possible that the PEN to be recycled will often be mixed with PET and other polymers and may be contaminated with impurities such as dyes, a method for the recovery and recycling of PEN from such mixtures is desired. Further, since the recycled PEN may be used for food packaging, it is desired that the recycling and recovery method involve conversion of PEN to a readily purifiable precursor so that contamination may be avoided.

SUMMARY OF THE INVENTION

Accordingly, one object of the present invention is to provide a novel method for the efficient recovery of useful materials from scrap poly(alkylene naphthalene-2,6-dicarboxylate) resins. Another object of the present invention is to provide a method for the recovery and recycling of PEN. Yet another object of the present invention is to provide a method for the efficient recovery of useful materials from scrap PEN mixtures which also contain PET and other polymers and may be also contaminated with impurities such as dyes. A further object of the present invention is to provide a method for the efficient recovery of useful materials from scrap PEN by its conversion to a readily purifiable precursor.

These objects and those which will become apparent in the course of the following specification have been achieved according to the present invention by the discovery that the alcoholysis of poly(alkylene) naphthalene-2,6-dicarboxylate) resins in the presence of a transesterification catalyst, on cooling and filtering, directly gives high yields of relatively pure dialkyl naphthalene-2,6-dicarboxylate esters which may be further purified by recrystallization. In particular, the present invention allows for the methanolysis of PEN to substantially pure dimethyl naphthalene-2,6-dicarboxylate (DMN). DMN is a particularly preferred precursor for the production of PEN.

A further aspect of the invention comprises the isolation of alkyl hydroxyalkyl naphthalene-2,6-dicarboxylates from the filtrate resulting from the alcoholysis of poly(alkylene naphthalene-2,6-dicarboxylate) resins. In particular, methanolysis of PEN gives a filtrate from which 2-hydroxyethyl methyl naphthalene-2,6-dicarboxylate (GMN) may be isolated. Alkyl hydroxyalkyl naphthalene-2,6-dicarboxylates and, particularly, GMN are useful materials for either further conversion to dialkyl naphthalene-2,6-carboxylates or reconversion to poly(alkylene naphthalene-2,6-dicarboxylate) resins. In addition, the present invention comprises a method for the production and isolation of dialkyl naphthalene-2,6-dicarboxylates from poly(alkylene naphthalene-2,6-dicarboxylate) mixtures which contain PET and other polymers and may be contaminated with impurities such as dyes.

Upon further study of the specification and claims, further objects and advantages of this invention will become apparent to those skilled in the art.

DETAILED DESCRIPTION OF THE PREFERRED EMBODIMENTS

The method of this invention is generally applicable to any poly(alkylene naphthalene-2,6-dicarboxylate). Such poly(alkylene naphthalene-2,6-dicarboxylate) resins contain repeating units of the structure:

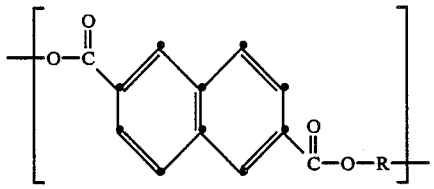

Thus, the diol component of the DNA-containing polyester may be any suitable diol, such ethylene glycol, butylene glycol, 1,4-cyclohexanedimethanol or 2,2-dimethyl-1,3-propanediol, and the like. It is particularly preferred to apply the present invention to PEN resins.

Any alcohol having in the range of 1 to 5 carbon atoms may be used for the alcoholysis. Thus, methanol, ethanol, propanol, isopropanol, butanol, sec-butanol, isobutanol, tertiary butanol, pentanol, sec-pentanol, isopentanol, tertiary pentanol and neopentanol all may be used for the alcoholysis. Additionally, diols such as ethylene glycol, propylene glycol, and butylene glycol may be used for the alcoholysis. The preferred method uses methanol for the alcoholysis, i.e., methanolysis.

Any suitable transesterification catalyst may be used in the method. Such catalysts include organic and inorganic compounds of metals such as titanium, manganese, antimony, zinc, tin, lead, calcium, cobalt, lithium, and combinations thereof. Specific catalysts include titanium tetraisopropoxide, titanium dioxide, zinc acetate, zinc acetyl acetonate, lead oxide, calcium oxide, lithium ethoxide, antimony trioxide, and manganese acetate. Generally, the acetates, chlorides, nitrates, sulfates, oxides, and alkoxides of one or more of the metals zinc, manganese, tin, lead, titanium, antimony, cobalt, and lithium are preferred. Particularly preferred are tin salts and titanium tetraisopropoxide. Most particularly preferred is zinc acetate.

The ratio of alcohol to polyester should be at least about 10 moles of alcohol per mole of repeating unit of the polyester. However, it is preferred that the alcohol be added in a 20 molar excess based on the moles of the repeating unit of the polyester. The transesterification catalyst is preferably added in amounts of from about 0.1 grams to about 0.2 grams per mole of repeating unit of polyester. The use of greater amounts of catalyst per repeating unit of polyester is also possible.

The alcoholysis may be conveniently carried out at a temperature in the range of from about 170° to 250° C. and a pressure in the range of from about 300 to 900 psig over a period of time ranging from about 0.5 to 3 hours. A temperature of about 220° C. and a pressure of about 750 psig are preferred.

The dialkyl naphthalene-2,6-dicarboxylates produced by the alcoholysis of the present invention may be isolated by any standard isolation technique. Thus, the dialkyl naphthalene-2,6-dicarboxylates may be collected as a precipitate from the cooled reaction mixture, they may be distilled from the reaction mixture, or the like. Preferred collection techniques include supernatent decantation after centrifugation and filtration. Filtration of the cooled reaction mixture is particularly preferred.

The isolated dialkyl naphthalene-2,6-dicarboxylates may be further purified by any standard purification method, such as distillation, gas chromatography, column chromatography, thin layer chromatography, liquid chromatography, high-pressure liquid chromatography, recrystallization, and the like. Recrystallization is the preferred method of purification.

Suitable recrystallization solvents include aromatic hydrocarbons having from one to four alkyl substituents on the aromatic nucleus. Preferred are toluene, ethylbenzene, n-propylbenzene, cumene, n-butylbenzene, isobutylbenzene, sec-butylbenzene, tert-butylbenzene, p-cymene, o-xylene, m-xylene, p-xylene, hemimellitene, pseudocumene, mesitylene, prehnitene, and isodurene. Particularly preferred are o-xylene, m-xylene, and p-xylene and mixtures thereof.

An advantage of the present invention is that poly(alkylene naphthalene-2,6-dicarboxylate) resins may be conveniently converted to a readily purified precursor of the polymer. Thus, heating a mixture of PEN chips with methanol and zinc acetate yielded a reaction mixture which on cooling afforded a high yield of relatively pure DMN (>98%) which was collected by filtration. Recrystallization from xylenes gave substantially pure (>99%) DMN. The DMN can be used as a starting material for the production of new PEN.

Another advantage of the present invention is that it may be applied to poly(alkylene naphthalene-2,6-dicarboxylate) resins which contain impurities such as dyes. For example, methanolysis of PEN chips which contain amber dye (for fabrication into beverage bottles) in the presence of zinc acetate gave a high yield of DMN which possessed only a slight purple-blue color. A single recrystallization of the DMN from xylene, without the use of decolorizing charcoal, yielded pure white crystals of DMN.

The present invention may also be applied to poly(alkylene naphthalene-2,6-dicarboxylate) resins mixed with other polymers which may be dyed. For example, heating a mixture of methanol, zinc acetate, PEN chips, and shredded black-dyed polyethylene, cooling the mixture, and filtration gave a high yield of DMN which could be easily separated from the shredded polyethylene by sieving. A single recrystallization from xylenes, with decolorizing charcoal, gave pure DMN suitable for reconversion to PEN.

A further advantage of the present invention is that it may be applied to mixtures of poly(alkylene naphthalene-2,6-dicarboxylate) and PET. After methanolysis of a mixture of PEN and PET chips and collection of the solid mixture of DMN and DMT by filtration, pure DMN and DMT were isolated by fractional vacuum distillation. Alternatively, the DMN and DMT may be separated by any conventional separation techniques such as fractional crystallization, gas chromatography, column chromatography, liquid chromatography, high-pressure liquid chromatography, and the like.

The present invention also comprises the isolation of alkyl hydroxyalkyl napthalene-2,6-dicarboxylates having the structure:

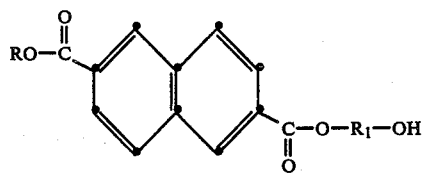

wherein R is $C_1$-$C_5$ alkyl, and $R_1$ is ethylene, butylene, 1,4-cyclohexylenedimethylene or 2,2-dimethyl-1,3-propylene, from the filtrate of the cooled alcoholysis reaction mixture. Such alkyl hydroxyalkyl naphthalene-2,6-dicarboxylates are suitable for reconversion to poly(alkylene naphthalene-2,6-dicarboxylate). For example, methanolysis of PEN and collection of the solid DMN by filtration gave a filtrate containing methanol, ethylene glycol, DMN, and GMN. Distillation of the methanol and water extraction of the ethylene glycol yielded a wet solid mixture of DMN and GMN. Recrystallization from xylene gave pure GMN. The pure GMN isolated in this manner is suitable for reconversion to PEN.

A further advantage of the present invention is that the crude uncrystallized alkyl hydroxyalkyl naphthalene-2,6-dicarboxylate can be conveniently converted to relatively pure dialkyl naphthalene-2,6-dicarboxylate. Thus, methanolysis of crude uncrystallized GMN in the presence of zinc acetate followed by filtration of the cooled reaction mixture yielded relatively pure DMN (>98%).

Other features of the invention will become apparent in the course of the following descriptions of exemplary embodiments which are given for illustration of the invention and are not intended to be limiting thereof.

EXAMPLES

Example 1

A mixture of 528 g of PEN chips, 2,000 mL of methanol and 0.4 g of zinc acetate was sealed in a stainless steel autoclave and brought to 220° C. with agitation supplied by rocking. The autogenous pressure created by the methanol was about 750 psig. After three hours of reaction, the heating was stopped and the reaction mixture was allowed to cool slowly to ambient temperature over a period of two hours while the rocking agitation was maintained. The reaction product, a slurry of DMN in the methanol solvent, was filtered to give 465 g of product which assayed at least 99% pure by gas-liquid chromatography. Recrystallization of this DMN once from mixed xylenes gave highly pure product which was satisfactory in all respects for conversion to new PEN polyester. The methanol of the filtrate was distilled at reduced pressure (20 torr, pot temperature raised at 60° C.) to give 160 g of a nonvolatile semisolid which analyzed as 69.4 weight % ehtylene glycol, 1.1% DMN and 17.6% GMN and 4.4% diethylene glycol. The ethylene glycol was readily extracted from the mixture with water to leave a wet solid which is 4.0% DMN and 70% GMN. Two recrystallizations of this solid from xylene gave pure GMN, m.p. 111°–112° C. The NMR and IR spectra of the material were in accord with the proposed structure;

Anal. calc'd for $C_{15}H_{14}O_5$: C, 65.68; H, 5.14.

Found: C, 65.86; H, 5.10. Exact mass by electron impact mass spectrometry: 274.0809; calc'd for $C_{15}H_{14}O_5$: 274.0837.

Example 2

The above experiment was repeated with 500 mL methanol, 0.1 g of zinc acetate and 132 g of PEN chips which were amber dyed for fabrication into beverage bottles. Workup of the reaction mixture gave 122.1 g of DMN which was a light purple-blue color and 40.6 g of an ethylene glycol/DMN/GMN mixture, wherein practically all of the coloration resided. A single recrystallization of the DMN from xylene, without use of decolorizing charcoal, yielded pure white crystals of DMN.

Example 3

Example 1 was repeated but the PEN chips also contained 48 g of black-dyed polyethylene shredded in small pieces. After the reaction mixture had cooled and the product slurry was filtered, the polyethylene was found to be present as polydisperse fragments in the DMN from which it was easily removed by sieving. None of the coloration in the polyethylene had migrated to the DMN or the ethylene glycol/DMN/GMN product fraction. Recrystallization from mixed xylenes, with decolorizing charcoal of a portion of the DMN, which had been mostly separated from the polyethylene residues by sieving, again gave pure DMN which was satisfactory in every way for reconversion to PEN polyester.

Example 4

The experimental conditions of Example 1 were applied to 264 g of PEN chips combined with 264 g of PET chips, 2,000 mL of methanol, and 0.4 g of zinc acetate. The white solid product isolated from the product mixture by filtration assayed 52.4 weight % DMN and 47.6 weight % DMT by gas-liquid chromatography and weighed 464 g. Distillation of 365 g of the DMN/DMT mixture at 50 torr gave two fractions (total weight=151 g) which were 99.6% and 99.9% DMT, b.p.=185° C. An intermediate fraction, b.p.=185°–200° C., weighed 30 g and two high boiling fractions, b.p.=265° C., weighed 49 g and 92 g and were 99.6% and 100% DMN, respectively. A pot residue (40 g), although discolored, assayed 99.1% DMN. Thus reisolation of DMN from a DMN/DMT mixture is readily effected. The DMN fractions collected were reconverted to PEN polyester which was the equivalent or better than polyester made from virgin DMN.

Example 5

Crude GMN, isolated as described in Example 1, may be converted to DMN by further methanolysis. Twenty grams of crude, unrecrystallized GMN were combined with 60 mL of methanol and 0.1 g of zinc acetate in an autoclave and held at 220° C. for three hours with magnetic stirring of the contents. After the cooling, the contents of the autoclave were filtered to yield, after methanol washing and drying, 15.41 g of DMN of 98.5% purity by gas chromatograpy (GC) (area %). Evaporation of the filtrates and washings yielded 5.98 g of residue which was 60.5% ethylene glycol and 18.9% GMN by GC.

Obviously, numerous modifications and variations of the present invention are possible in light of the above teachings. It is therefore to be understood that within the scope of the appended claims, the invention may be practiced otherwise than as specifically described herein.

I claim:

1. A process for the formation of dialkyl naphthalene-2,6-dicarboxylates from a polymer or polymer mixture containing poly(alkylene naphthalene-2,6-dicarboxylate), said process comprising heating a mixture comprising:
   (i) said polymer or polymer mixture,
   (ii) at least one alcohol having 1 to 5 carbon atoms or a diol having 1 to 5 carbon atoms, and
   (iii) at least one transesterification catalyst,
wherein said heating is carried out under suitable conditions of temperature and pressure for a time sufficient to at least partially alcoholize said mixture.

2. The process of claim 1 further comprising recovering said dialkyl naphthalene-2,6-dicarboxylate by
   (a) cooling said partially alcoholized mixture so as to precipitate substantial quantities of said dialkyl naphthalene-2,6-dicarboxylate; and
   (b) isolating said precipitated dialkyl naphthalene-2,6-dicarboxylate from said cooled mixture.

3. The process of claim 2, further comprising recrystallizing said isolated dialkyl naphthalene-2,6-dicarboxylate from an aromatic hydrocarbon solvent.

4. The process of claim 3, wherein said aromatic hydrocarbon solvent is a mixture of xylene isomers.

5. The process of claim 1, wherein said polymer mixture comprises substantial quantities of poly(alkylene terephthalate) and poly(alkylene naphthalene-2,6-dicarboxylate).

6. The process of claim 2 wherein said cooling step precipitates a mixture of a terephthalic acid ester and dialkyl naphthalene-2,6-dicarboxylate.

7. The process of claim 6 wherein said precipitated mixture of terephthalic acid ester and dialkyl naphthalene-2,6-dicarboxylate is subjected to fractional distillation under reduced pressure.

8. The process of claim 1, wherein at least 10 moles of said alcohol are employed per mole of repeating unit of said polymer.

9. The process of claim 8, wherein said alcohol is methanol.

10. The process of claim 1, wherein said transesterification catalyst is one or more members selected from the group consisting of zinc acetate, tin salts, and titanium tetraisopropoxide.

11. The process of claim 1, wherein at least 0.1 g of said transesterification catalyst is employed per mole of repeating unit of polymer.

12. The process of claim 1, wherein said suitable conditions comprise a temperature in the range of from about 170° to 250° C., a pressure in the range of from about 300 to 900 psig and a reaction time in the range of from about 0.5 to 3 hours.

13. The process of claim 1, wherein said poly(alkylene naphthalene-2,6-dicarboxylate) is at least one member selected from the group consisting of poly(ethylene naphthalene-2,6-dicarboxylate), poly(butylene naphthalene-2,6-dicarboxylate), and poly(1,4-cyclohexylenedimethylene naphthalene-2,6-dicarboxylate).

14. A process for the recovery of dialkyl naphthalene-2,6-dicarboxylate from a polymer or polymer mixture containing poly(alkylene naphthalene-2,6-dicarboxylate), said process comprising isolating precipitated dialkyl naphthalene-2,6-dicarboxylate from a cooled reaction mixture which comprises:
   (i) said polymer or polymer mixture,
   (ii) at least one alcohol having 1 up to 5 carbon atoms, and
   (iii) at least one transesterification catalyst; wherein said reaction mixture has been previously subjected to suitable conditions of temperature and pressure for a time sufficient to at least partially alcoholize the reaction mixture.

15. The process of claim 14, further comprising recrystallizing said isolated dialkyl naphthalene-2,6-dicarboxylate from an aromatic hydrocarbon solvent.

16. The process of claim 14, wherein at least 10 moles of said alcohol are employed per mole of repeating unit of said polymer.

17. The process of claim 16, wherein said alcohol is methanol.

18. A method for producing alkyl hydroxyalkyl naphthalene-2,6-dicarboxylate esters of the structure:

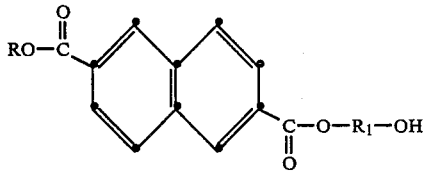

wherein R is $C_1$–$C_5$ alkyl, and $R_1$ is ethylene, butylene, 1,4-cyclohexylenedimethylene or 2,2-dimethyl-1,3-propylene; said process comprising contacting a polymer having repeating units of the structure:

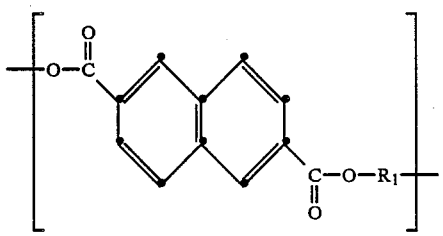

with an alcohol having the formula R—OH, and at least one transesterification catalyst under suitable conditions to produce said alkyl hydroxyalkyl naphthalene-2,6-dicarboxylate.

19. The method of claim 18, wherein R is methyl and $R_1$ is ethylene.

20. The method of claim 18, wherein said suitable conditions comprise a temperature in the range of from about 170° to 250° C., a pressure in the range of from about 300 to 900 psig, and a reaction time in the range of from about 0.5 to 3.0 hours.

21. An alkyl hydroxyalkyl naphthalene-2,6-dicarboxylate having the structure:
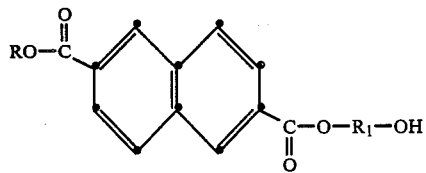
wherein R is $C_1$–$C_5$ alkyl and $R_1$ is ethylene, butylene, 1,4-cyclohexylenedimethylene or 2,2-dimethyl-1,3-propylene.
22. The alkyl hydroxyalkyl naphthalene-2,6-dicarboxylate of claim 21, wherein R is methyl and $R_1$ is ethylene.
* * * * *